US009877848B2

(12) United States Patent
Ikebe

(10) Patent No.: US 9,877,848 B2
(45) Date of Patent: Jan. 30, 2018

(54) FINGER JOINT DRIVING DEVICE

(71) Applicant: Seiko Epson Corporation, Tokyo (JP)

(72) Inventor: Tomo Ikebe, Suwa (JP)

(73) Assignee: Seiko Epson Corporation (JP)

( * ) Notice: Subject to any disclaimer, the term of this patent is extended or adjusted under 35 U.S.C. 154(b) by 411 days.

(21) Appl. No.: 14/636,313

(22) Filed: Mar. 3, 2015

(65) Prior Publication Data

US 2015/0250621 A1 Sep. 10, 2015

(30) Foreign Application Priority Data

Mar. 5, 2014 (JP) ................. 2014-042452

(51) Int. Cl.
*A61H 1/00* (2006.01)
*A61F 2/58* (2006.01)
*A61F 5/01* (2006.01)

(52) U.S. Cl.
CPC .............. *A61F 2/586* (2013.01); *A61F 5/013* (2013.01); *A61F 2005/0155* (2013.01)

(58) Field of Classification Search
CPC .............. A61H 1/0288; A61H 2201/14; A61H 2201/1207; A61H 2201/1676; A61H 2201/165; A61H 2201/1635; A61F 2/586; A61F 5/013; A61F 2005/0155
See application file for complete search history.

(56) References Cited

U.S. PATENT DOCUMENTS

| | | | | |
|---|---|---|---|---|
| 5,328,448 A * | 7/1994 | Gray, Sr. | ............... | A61H 1/0288 482/44 |
| 5,376,091 A * | 12/1994 | Hotchkiss | ............... | A61B 17/62 602/22 |
| 6,502,577 B1 * | 1/2003 | Bonutti | ............... | A61F 5/013 128/898 |
| 6,622,575 B1 | 9/2003 | Nagata | | |
| 2014/0288664 A1 | 9/2014 | Miyazawa | | |
| 2015/0164660 A1 * | 6/2015 | Will | ............... | A61F 2/68 623/26 |
| 2015/0223959 A1 * | 8/2015 | Cempini | ............... | A61H 1/0285 602/22 |
| 2016/0015590 A1 * | 1/2016 | Arata | ............... | B25J 9/0006 623/64 |
| 2016/0296345 A1 * | 10/2016 | Deshpande | ............... | A61H 1/0288 |

FOREIGN PATENT DOCUMENTS

| | | |
|---|---|---|
| JP | 2001-021427 A | 1/2001 |
| JP | 2002-182817 A | 6/2002 |
| JP | 2002-345861 A | 12/2002 |
| JP | 2005-073714 A | 3/2005 |
| JP | 2008-126331 A | 6/2008 |
| JP | 2011-115248 A | 6/2011 |
| JP | 2014-184027 A | 10/2014 |
| WO | WO-2010-095619 A1 | 8/2010 |

* cited by examiner

*Primary Examiner* — Steven Douglas

(74) *Attorney, Agent, or Firm* — Harness, Dickey & Pierce, P.L.C.

(57) ABSTRACT

A finger joint driving device includes a first base portion that is mounted on an index finger, a pressure sensor that is provided between the first base portion and the index finger when the first base portion is mounted on the index finger, and a contact portion that is provided between the pressure sensor and the index finger and comes in contact with the pressure sensor in the mounted state. In addition, durometer hardness of the contact portion which is measured based on JIS K 6253 is equal to or greater than 50.

8 Claims, 7 Drawing Sheets

FINGER JOINT DRIVING DEVICE

BACKGROUND

1. Technical Field

The present invention is related to a finger joint driving device.

2. Related Art

A finger joint driving device which is mounted on a hand and assists movement of a finger in the mounted state, that is, which bends and stretches a finger joint has been known (for example, refer to JP-A-2002-345861). The finger joint driving device disclosed in JP-A-2002-345861 is provided with a slide bracket which is disposed on a back of the hand in the mounted state, a third connection member which is provided on the end side of the finger with respect to the slide bracket, and a third rear arm and a third front arm which are turnably provided with respect to the third connection member. In addition, the slide bracket slides, thus the third connection member slides, and together with this, the third rear arm and the third front arm turn in the opposite direction to each other, and thereby it is possible to bend the third joint of the finger.

The finger joint driving device is also configured to assist the movement of the finger by detecting, for example, the movement of a user's finger and driving the finger joint driving device so as to assist the movement. In this case, a configuration is exemplified in which a pressure sensor is provided between the finger and a portion which is fixed to the finger of the finger joint driving device (hereinafter, referred to as a "finger mounting portion"). Accordingly, it is possible to detect the force applied to the finger mounting portion from the finger. Then, it is possible to assist the movement of the finger by driving the finger joint driving device based on a detection result.

However, the finger is relatively flexible and thus is deformed if it is bent or stretched. Due to this deformation, the force which is applied to the finger mounting portion from the finger is dispersed. Therefore, it is difficult to accurately detect the force which is applied to the finger mounting portion from the finger.

SUMMARY

An advantage of some aspects of the invention is to provide a finger joint driving device capable of accurately detecting the force which is applied to the finger mounting portion from the finger when the user uses the finger joint driving device mounted on the hand.

The advantage can be attained by the following application example of the invention.

Application Example 1

This application example is directed to a finger joint driving device including: a finger mounting portion that is mounted on a finger; a force detection unit that is provided between the finger mounting portion and the finger when the finger mounting portion is mounted on the finger; and a contact portion that is provided between the force detection unit and the finger and comes in contact with the force detection unit in the mounted state, in which durometer hardness of the contact portion which is measured based on JIS K 6253 is equal to or greater than 50.

With this configuration, it is possible to make the hardness of the contact portion be greater than the hardness of the finger. Therefore, it is possible to efficiently transfer the force which is applied to the finger mounting portion from the finger to the force detection unit. Thus, it is possible to accurately detect the force which is applied to the finger mounting portion from the finger.

Application Example 2

In the finger joint driving device according to the application example described above, it is preferable that Rockwell hardness of the contact portion which is measured based on JIS K 7202 is equal to or greater than 80.

With this configuration, it is possible to make the hardness of the contact portion be greater than the hardness of the finger. Therefore, it is possible to more efficiently transfer the force which is applied to the finger mounting portion from the finger to the force detection unit.

Application Example 3

In the finger joint driving device according to the application example described above, it is preferable that at least one of the contact portion and the finger mounting portion includes a projection portion projected to the force detection unit.

With this configuration, the contact portion can reliably come in contact with the force detection unit, and thus it is possible to efficiently detect the force which is applied to the finger mounting portion from the finger.

Application Example 4

In the finger joint driving device according to the application example described above, it is preferable that the projection portion has a curved surface which is curved toward the force detection unit.

With this configuration, it is possible to reduce a contact area of the force detection unit and the contact portion as much as possible. Therefore, it is possible to more efficiently detect the force which is applied to the finger mounting portion from the finger.

Application Example 5

In the finger joint driving device according to the application example described above, it is preferable that the contact portion is formed into a plate shape which is curved toward one direction.

With this configuration, the contact portion follows the shape of the finger in the mounted state. Therefore, the user can avoid feeling tightness and discomfort.

Application Example 6

In the finger joint driving device according to the application example described above, it is preferable that the force detection unit and the contact portion are positioned on the back of the hand of the finger in the mounted state.

With this configuration, is possible to more accurately detect the force which is applied to the finger mounting portion from the finger.

Application Example 7

In the finger joint driving device according to the application example described above, it is preferable that the finger mounting portion includes a finger mounting portion main body that is positioned on the back of the hand of the finger and a fixing portion that comes in contact with the palm of the hand of the finger to fix the finger mounting portion main body to the finger in the mounted state.

With this configuration, it is possible to stably fix the finger to the finger mounting portion, thereby stably detecting the force which is applied to the finger mounting portion from the finger.

Application Example 8

In the finger joint driving device according to the application example described above, it is preferable that a pair of the force detection unit and a pair of the contact portion are provided via the finger in the mounted state, in which one of the force detection unit and one of the contact portion are provided on the finger mounting portion main body side, and the other force detection unit and the other contact portion are provided on the fixing portion side.

With this configuration, each of the pair of force detection units can stably detect the force which is applied to the finger mounting portion main body from the finger. In addition, since a degree of bending and stretching of the finger is determined based on a difference between the forces detected by the force detection units, it is possible to accurately detect the force.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, a finger joint driving device according to the invention will be described in detail based on preferred embodiments with reference to drawings.

First Embodiment

Figure 1:
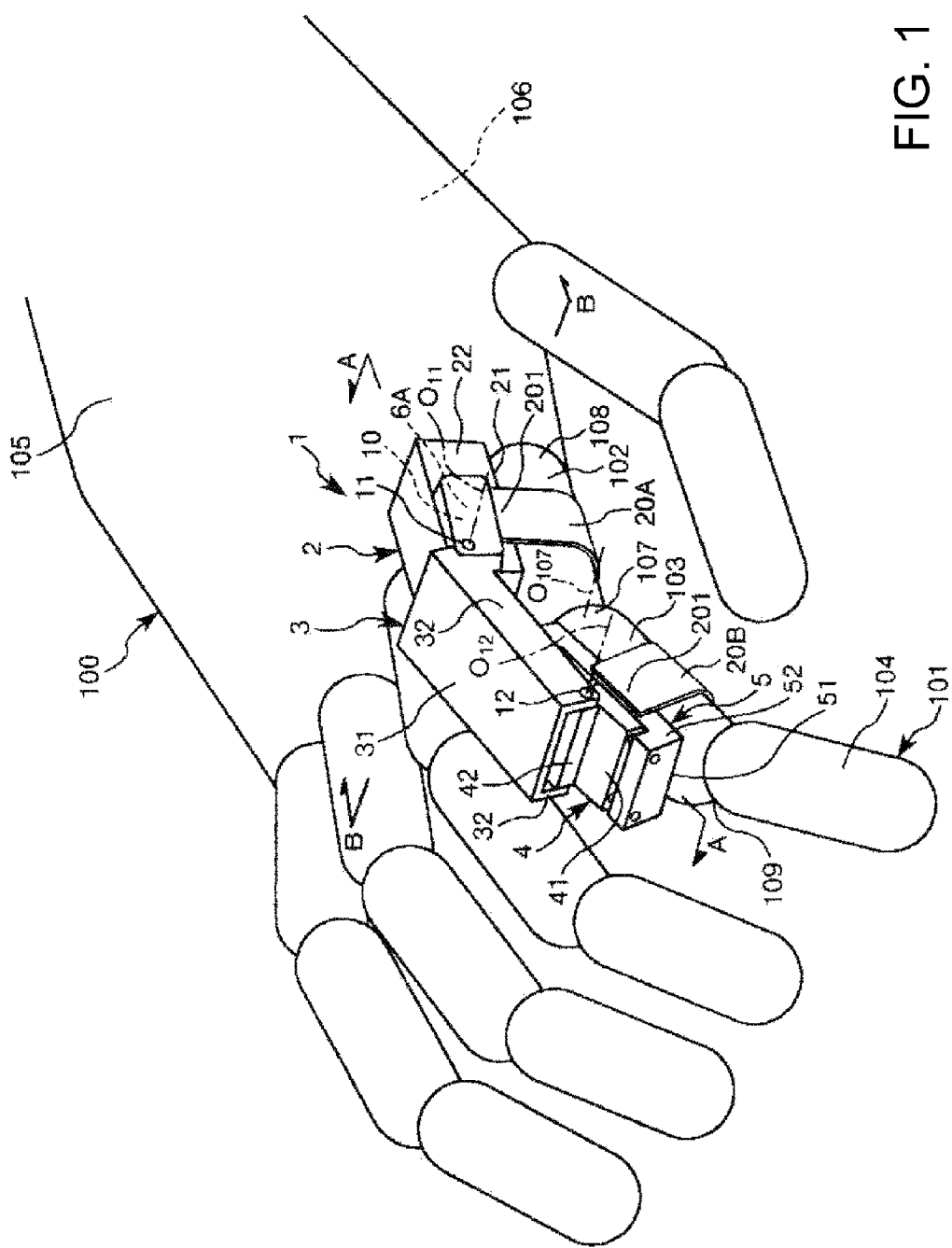
FIG. 1 is a perspective view illustrating a usage state of a finger joint driving device (a first embodiment) according to the invention.
Figure 2:
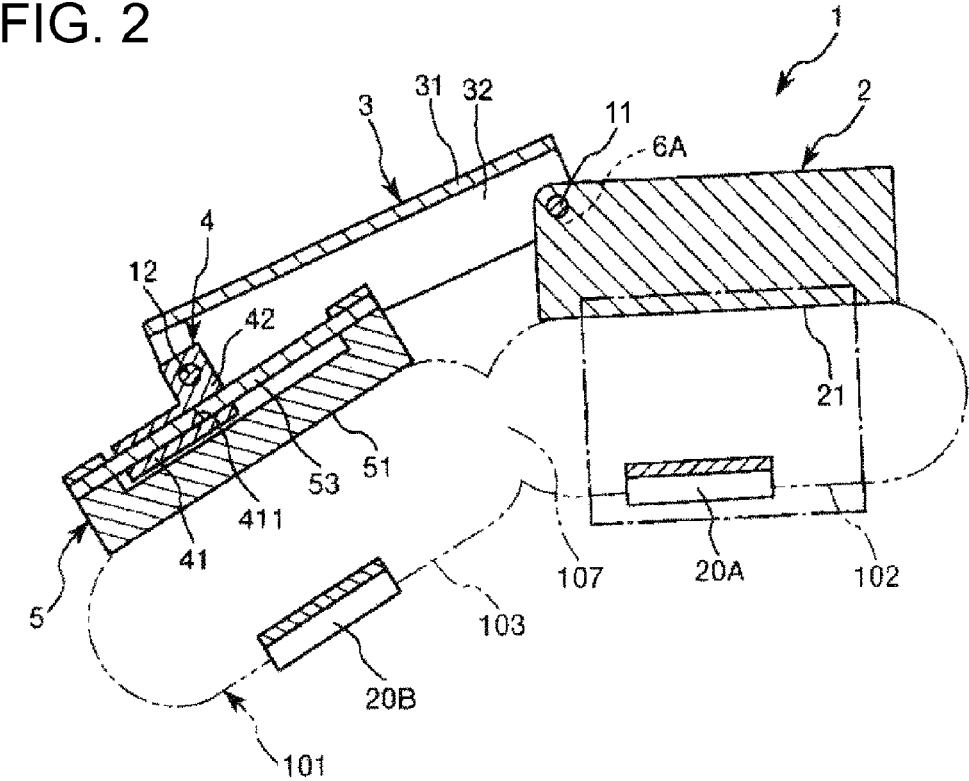
FIG. 2 is a cross-sectional view taken along line A-A in FIG. 1.
Figure 3:
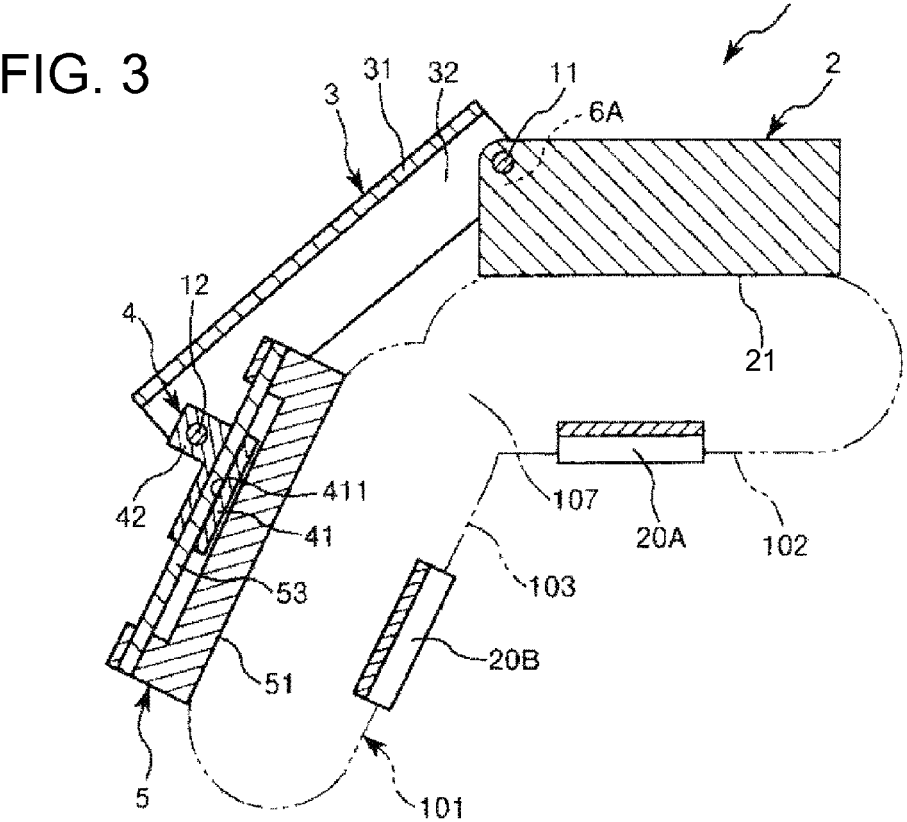
FIG. 3 is a cross-sectional view illustrating a finger which is bent in the state illustrated in FIG. 2.
Figure 4:
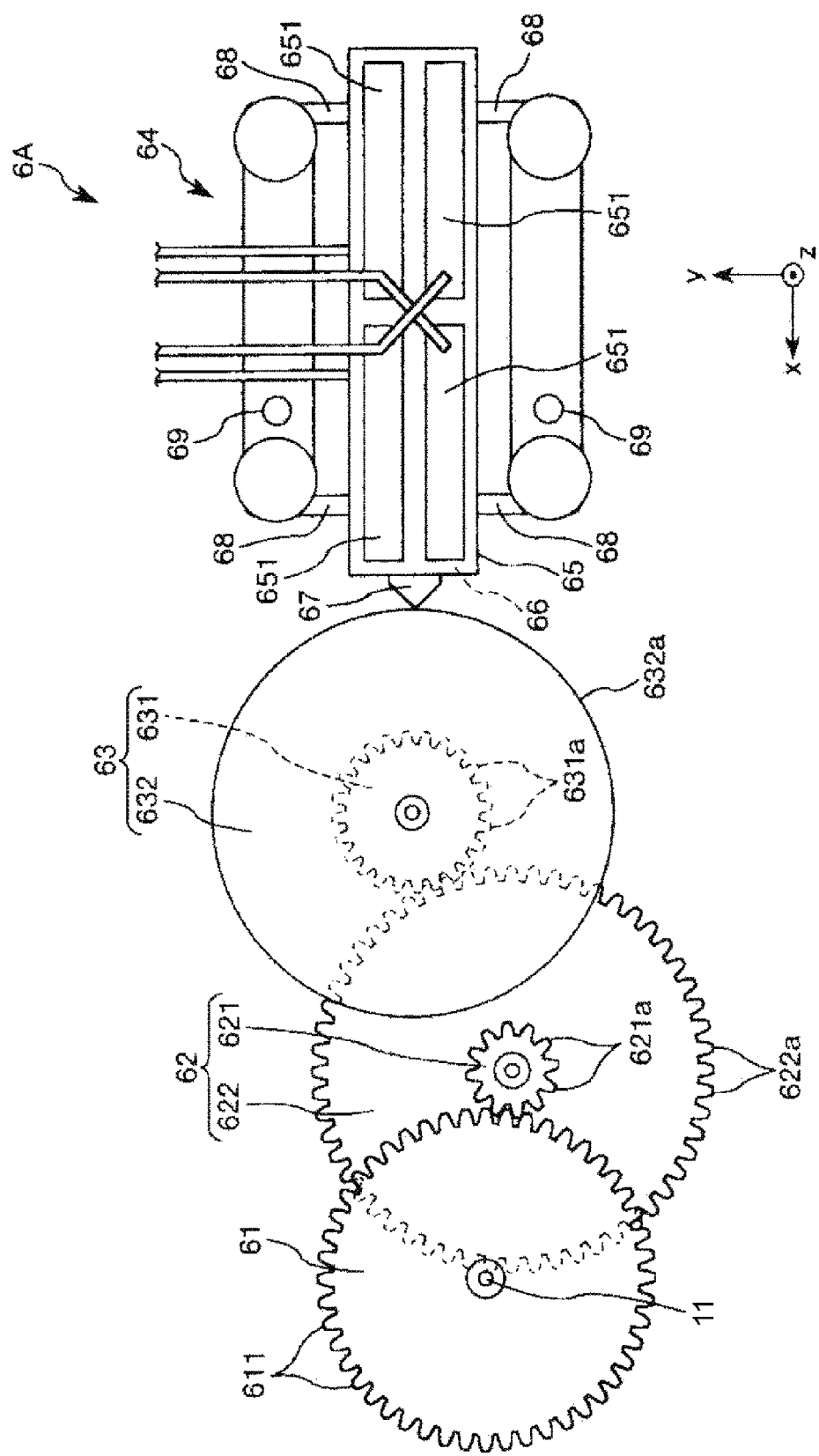
FIG. 4 is a plan view of a driving unit provided in the finger joint driving device in FIG. 1.
Figure 5C:
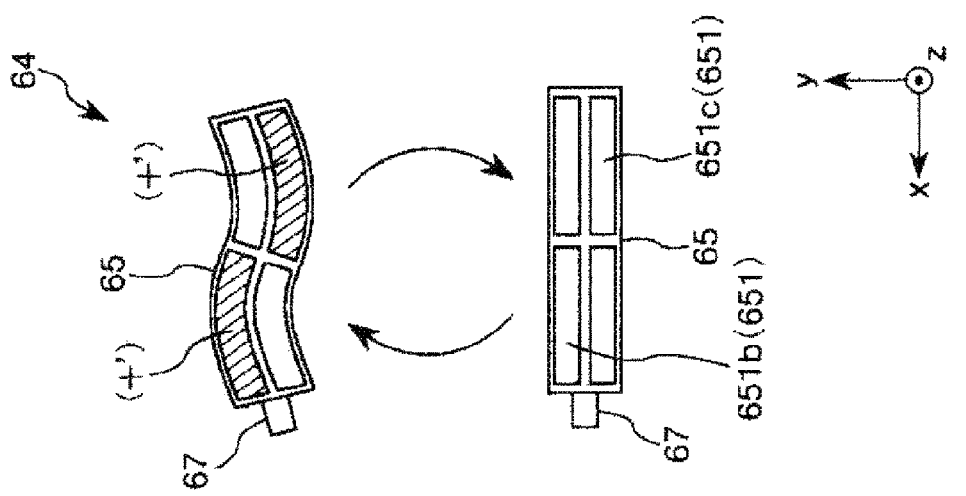
FIGS. 5A through 5C are explanatory diagrams illustrating operating principles of the driving unit.
Figure 5B:
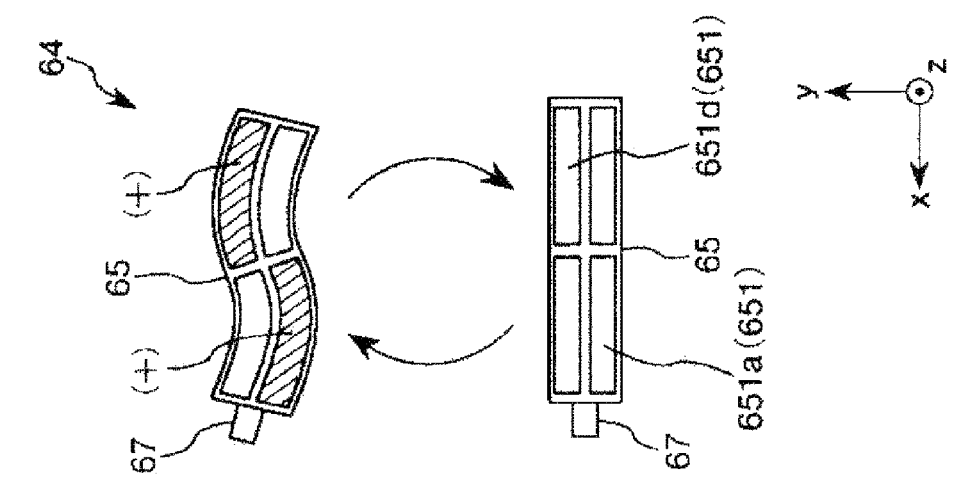
Figure 5A:
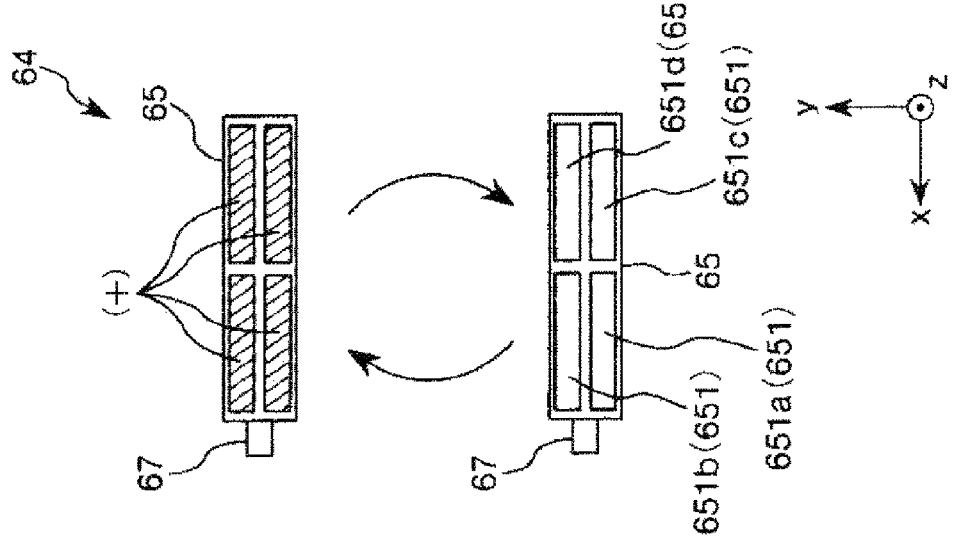
Figure 6:
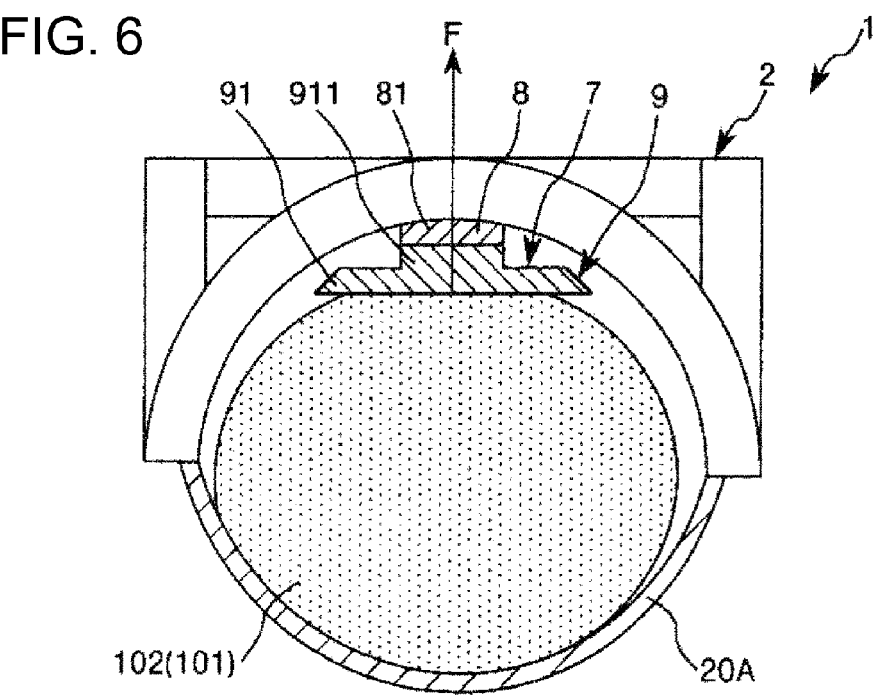
FIG. 6 is a cross-sectional view taken along line B-B in FIG. 1.
Figure 7:
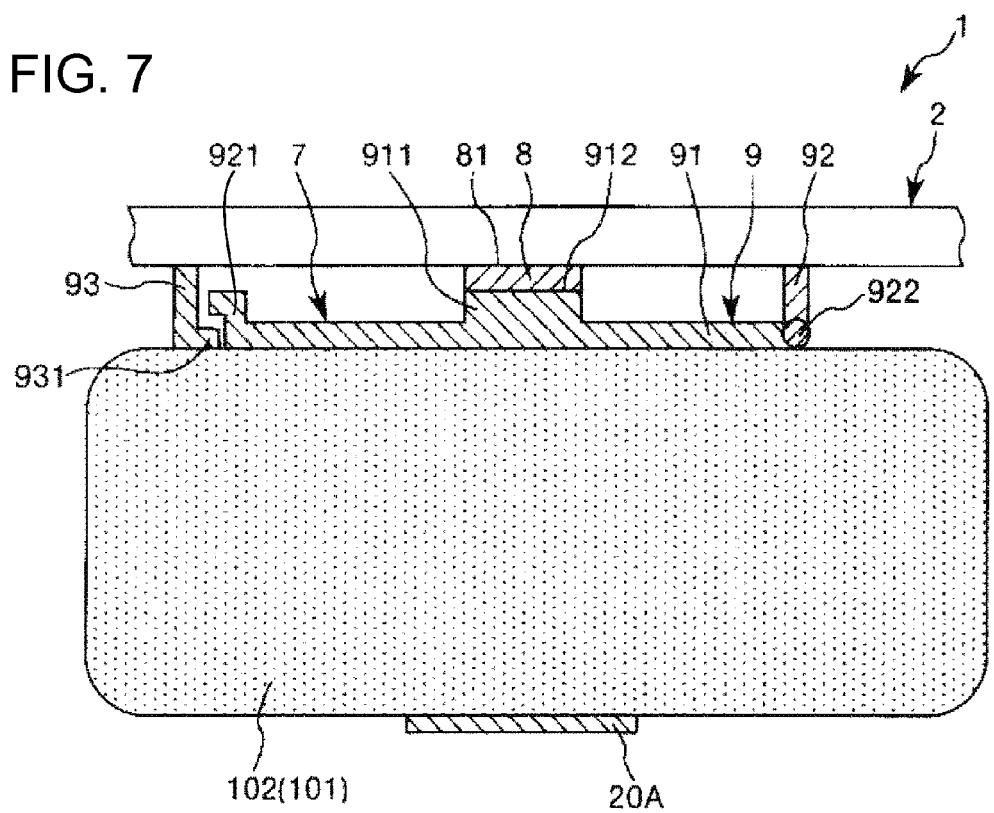
FIG. 7 is an enlarged detail view of an area indicated by a dashed line in FIG. 2.

FIG. 1 is a perspective view illustrating a usage state of a finger joint driving device (first embodiment) according to the invention. FIG. 2 is a cross-sectional view taken along line A-A in FIG. 1. FIG. 3 is a cross-sectional view illustrating a finger which is bent in the state illustrated in FIG. 2. FIG. 4 is a plan view of a driving unit included in the finger joint driving device as illustrated in FIG. 1. FIGS. 5A to 5C are explanatory diagrams illustrating operating principles of the driving unit. FIG. 6 is a cross-sectional view taken along line B-B in FIG. 1. FIG. 7 is an enlarged detail view of an area indicated by a dashed line in FIG. 2.

Meanwhile, hereinafter, for the sake of convenience of description, fingers are schematically illustrated, and the obliquely left downward side is referred to as the "end side of the finger" and the opposite side which is the obliquely right upward side is referred to as the "wrist side" in FIG. 1, and the left side is referred to as "the end side of the finger" and the opposite side which is the right side is referred to as the "wrist side" in FIG. 2 and FIG. 3. In addition, the wrist front side is referred to as the "front side" in the drawing and the opposite side which is the back side is referred to as the "rear side" in FIG. 4. In addition, the upper side is referred to as "above" and the lower side is referred to as "under" in FIG. 6 and FIG. 7. Then, in order to facilitate understanding, the pressure sensitive unit is omitted in FIG. 1 to FIG. 3.

The finger joint driving device 1 illustrated in FIG. 1 is mounted on hand 100 of a person, for example, who has trouble bending and stretching the finger due to an accident or illness, who has a weak grip, or who has weakened force because of age, that is, mounted on the index finger 101 in the embodiment. In addition, the finger joint driving device 1 allows the finger joint of the index finger 101 to bend and stretch in the mounted state, that is, the finger joint driving device 1 is a device which is used to assist turning of the finger joint. The finger joint driving device 1 is provided with a first base portion (a finger mounting portion main body) 2, a first link portion 3, a second link portion 4, and a second base portion 5, and a pressure sensitive unit 7. In addition, the first base portion 2, the first link portion 3, the second link portion 4 and the second base portion 5 are connected to each other in order from the wrist side toward the end side of the finger. Hereinafter, the configuration of the respective portions will be described.

As illustrated in FIG. 1 to FIG. 3, the first base portion 2 is disposed on the back of the hand 105 side of the knuckle 102 of the index finger 101 in the mounted state, that is, on the upper side in the drawings.

The first base portion 2 is a member of which an external shape is a flat block shape. In addition, a surface 21 on the knuckle 102 side of the first base portion 2 is bent along the shape of the knuckle 102. Accordingly, the first base portion 2 is disposed on the knuckle 102 without giving a sense of discomfort to a user (a wearer) of the finger joint driving device 1. Further, the first base portion 2 is stably disposed with respect to the knuckle 102.

In addition, the first base portion 2 is mounted on the knuckle 102 of the index finger 101 by using a mounting band (a fixing portion) 20A. The mounting band 20A is configured of a length adjustable belt and an end portion 201 at each end is fixed to each side surface 22 of the first base portion 2. The mounting band 20A can allow the first base portion 2 to be adhered to the knuckle 102 by going around a palm of the hand 106 side of the knuckle 102 of the index finger 101, that is, the back of the diagram in FIG. 1 to FIG. 3. Therefore, it is possible to prevent the first base portion 2 from being separated from the knuckle 102.

Such a first base portion 2 and the mounting band 20A configure the finger mounting portion.

As illustrated in FIG. 1 (the same is applied to FIG. 2 and FIG. 3), the second base portion 5 is disposed on the end side of the finger from the first base portion 2 in the mounted state, that is, disposed on the back of the hand 105 side of the middle phalanx 103 of the index finger 101. Accordingly, as will be described later, it is possible to bend and stretch the proximal interphalangeal joint (the second joint) 107 between the knuckle 102 and the middle phalanx 103 of the index finger 101 by using the finger joint driving device 1 (refer to FIG. 2 and FIG. 3).

The second base portion 5 is a member of which an external shape is a flat block shape and cross section is a concave shape. The surface 51 which comes into contact with the middle phalanx 103 of the second base portion 5 is preferably bent along the shape of the middle phalanx 103. Accordingly, the second base portion 5 is disposed on the middle phalanx 103 without giving a sense of discomfort to the user of the finger joint driving device 1. Further, the second base portion 5 is stably disposed with respect to the middle phalanx 103.

In addition, the second base portion 5 is mounted on the middle phalanx 103 of the index finger 101 by using a mounting band 20B. The mounting band 20B is configured of a length adjustable belt similar to the mounting band 20A and the end portions 201 at each end is fixed to the side surface 52 of the second base portion 5. The mounting band 20B can allow the second base portion 5 to be adhered to the middle phalanx 103 by going around a palm of the hand 106 side of the middle phalanx 103 of the index finger 101. Therefore, it is possible to prevent the second base portion 5 from being separated from the middle phalanx 103.

As illustrated in FIG. 1, the first link portion 3 is provided on the end side of the finger of the first base portion 2. The first link portion 3 is a member of which the total length is greater than the total length of the first base portion 2 or the first base portion 2. The first link portion 3 includes a top plate 31 and side walls 32 which project from both edge portions of the top plate 31. In addition, the two side walls 32 interpose the first base portion 2 therebetween.

In addition, each of the side walls 32 and the side surface 22 of the first base portion 2 are connected to each other via a turning support portion 11. The turning support portion 11 is configured to have a shaft which is provided on one of the side wall 32 and the first base portion 2 and a bearing in which a shaft is inserted and is provided on the other of the side wall 32 and the first base portion 2. In addition, when a turning axis $O_{107}$ is assumed when the proximal interphalangeal joint 107 is turned by bending and stretching, a turning axis $O_{11}$ of the turning support portion 11 is in parallel with the turning axis $O_{107}$. With such a configuration, the first link portion 3 can be turned around the turning axis $O_{11}$ with respect to the first base portion 2 by the turning support portion 11.

The second link portion 4 is provided on the end side of the finger of the first link portion 3. The second link portion 4 includes a sliding portion 41 sliding with respect to the second base portion 5 and a projection portion 42 which projects from a portion of the upper surface on the sliding portion 41.

As illustrated in FIG. 2 and FIG. 3, the sliding portion 41 is formed into a cylindrical shape, and includes a cylindrical hollow portion 411. The rail portion 53 of the second base portion 5 is inserted into the hollow portion 411 of the sliding portion 41. Meanwhile, the total length of the rail portion 53 is sufficiently longer than the total length of the sliding portion 41, for example, it is preferably 1.5 times to 3 times the total length of the sliding portion 41, and more preferably 1.7 times to 2.3 times.

Since the sliding portion 41 slides while being guided by the rail portion 53, the second base portion 5 can relatively approach with respect to and be separated from the first base portion 2. FIG. 2 illustrates a state where the second base portion 5 approaches with respect to the first base portion 2 and FIG. 3 illustrates a state where the second base portion 5 is separated from the first base portion 2.

The projection portion 42 is interposed between the two side walls 32 of the first link portion 3. Then, the projection portion 42 and each of the side walls 32 are connected to each other via a turning support portion 12. The turning support portion 12 is configured to have a shaft which is provided on one of the projection portion 42 and the side wall 32 and a bearing in which the shaft is inserted and is provided on the other of the projection portion 42 and the side wall 32. In addition, a turning axis $O_{12}$ of the turning support portion 12 is in parallel with the turning axis $O_{107}$. With such a configuration, similar to the first link portion 3, the second link portion 4 can be turned around the turning axis $O_{12}$ which is in parallel with the turning axis $O_{107}$ by the turning support portion 12. Since the turning axis $O_{11}$ and the turning axis $O_{12}$ are in parallel with the turning axis $O_{107}$, it is possible to easily bend and stretch the proximal interphalangeal joint 107 by the finger joint driving device 1 while preventing unnecessary force from being applied to the proximal interphalangeal joint 107.

Configuration materials of the first base portion 2, the first link portion 3, the second link portion 4, and the second base portion 5 are not particularly limited and, for example, various kinds of resin materials such as polyethylene or various kinds of metallic materials such as aluminum can be used. In addition, configuration materials of the mounting bands 20A and 20B are not particularly limited; for example, various rubber materials such as silicone rubber can be used.

In addition, as illustrated in FIG. 1, the finger joint driving device 1 is further provided with the driving unit (the first driving unit) 6A and a control unit 10.

The driving unit 6A is a mechanical portion which functions for driving the first link portion 3 to be turned via the turning support portion 11.

As illustrated in FIG. 4, the driving unit 6A includes a first rotor 61 which is concentrically connected to the shaft of the turning support portion 11, a second rotor 62 which causes the first rotor 61 to rotate, a third rotor 63 which causes the second rotor 62 to rotate, and a piezoelectric motor 64 which causes the third rotor 63 to rotate.

The first rotor 61 is formed into a disk shape and is a gear including a tooth 611 at the external edge portion thereof.

The second rotor 62 includes a small gear 621 and a large gear 622. The small gear 621 includes a tooth 621a which is engaged with the tooth 611 of the first rotor 61. The large gear 622 is a gear of which a diameter of a base circle is larger than a diameter of a base circle of the small gear 621. The large gear 622 is concentrically disposed with the small gear 621, and is connected (fixed) to the rear side of the small gear 621.

The third rotor 63 includes a small gear 631 and a large disk portion 632. The small gear 631 includes a tooth 631a which is engaged with a tooth 622a of the large gear 622. The large disk portion 632 is formed into a disk shape, and the diameter thereof is larger than the diameter of the base circle of the small gear 631. The large disk portion 632 is concentrically disposed with the small gear 631, and is connected to the front side the small gear 631.

As illustrated in FIG. 4, the piezoelectric motor 64 includes a piezoelectric material exerting a piezoelectric effect, and is a stacked body which is configured to have two sheet-like piezoelectric elements 65 and a shim plate 66 which is formed of a metal flat plate and interposed between the piezoelectric elements 65 and bonded thereto. Hereinafter, the lateral direction of the piezoelectric motor 64 is referred to as an "x direction", the width direction of the piezoelectric motor 64 which is orthogonal to the x direction is referred to as a "y direction", and the thickness direction of the piezoelectric motor 64 which is orthogonal to the x direction and the y direction is referred to as a "z direction".

Each of the piezoelectric elements 65 is provided with four electrodes 651 so as to apply the voltage to the piezoelectric element 65. These electrodes 651 are disposed in a matrix state of two lines and two rows on the piezoelectric element 65, and are electrically connected to batteries (not shown) such as button batteries as a power supply source.

In addition, the shim plate 66 which is made of metal not only reinforces the piezoelectric element 65 but also serves as a common electrode for applying the voltage to the piezoelectric element 65, and is grounded.

An end portion of the piezoelectric motor 64 in the x direction is provided with a convex portion 67. The convex portion 67 is integrally formed with the shim plate 66.

Four supporting portions 68, which support the piezoelectric motor 64 in a state of biasing toward the side on which the convex portion 67 is provided, are provided on both side surfaces of the piezoelectric motor 64 which face the y direction. These supporting portions 68 are integrally formed with the shim plate 66 and disposed on four corners of the shim plate 66 which is formed into a rectangular shape. Meanwhile, it is preferable that the supporting portions 68 which are adjacent in the x direction be connected to each other via a connection plate 69.

The operating principles of the piezoelectric motor 64 in such a configuration will be described with reference to FIGS. 5A to 5C.

The piezoelectric motor 64 is operated by an elliptical motion of the convex portion 67 of the piezoelectric motor 64 when the electrodes 651 of the respective piezoelectric motors 64 are periodically applied with the voltage. The convex portion 67 of the piezoelectric motor 64 performs the elliptical motion due to the following reason. Note that the electrodes 651 which are provided in the piezoelectric elements 65 are the same except for the disposition place, and thus the front side of the electrode 651 of the piezoelectric element 65 will be representatively described.

First, as is well known, the piezoelectric element 65 including the piezoelectric material has a property of extension when a positive voltage is applied to the piezoelectric element 65. Accordingly, as illustrated in FIG. 5A, when the positive voltage is applied to all of the four electrodes 651, and then the applied voltage is repeatedly canceled at a particular frequency, the piezoelectric motor 64 (the piezoelectric element 65) can generate a kind of resonance phenomenon in which the piezoelectric motor extends and contracts in the x direction. Meanwhile, an operation in which the piezoelectric motor 64 repeatedly extends and contracts in the x direction is referred to as an "extension and contraction vibration", and the direction in which the piezoelectric motor 64 extends and contracts (the ±x direction in the drawings) is referred to as an "extension and contraction direction".

In addition, as illustrated in FIG. 5B or FIG. 5C, when two electrodes 651 which are positioned by each other on a diagonal line (a pair of an electrode 651a and an electrode 651d or a pair of an electrode 651b and an electrode 651c) are assumed to be a pair and the voltage at a particular frequency is applied to the two electrodes 651, the piezoelectric motor 64 (the piezoelectric element 65) can generate a kind of resonance phenomenon in which the tip end portion (a portion with which the convex portion 67 is provided) in the x direction moves in the vertical direction (the y direction) in the drawing. For example, as illustrated in FIG. 5B, when the positive voltage is periodically applied to the pair of the electrode 651a and the electrode 651d, the piezoelectric motor 64 repeatedly operates the tip end portion in the x direction to move in the lower direction. In addition, as illustrated in FIG. 5C, when the positive voltage is periodically applied to the pair of the electrode 651b and the electrode 651c, the piezoelectric motor 64 repeatedly operates the tip end portion in the x direction to move in the vertical direction. Such an operation of the piezoelectric motor 64 is referred to as a "bending vibration". Hereinafter, the direction (the ±y direction) in which the piezoelectric motor 64 performs the bending vibration is referred to as a "bending direction".

In addition, it is possible to concurrently derive a resonance of the "extension and contraction vibration" with a resonance of the "bending vibration" by appropriately selecting physicality of the piezoelectric element 65 and dimensions of the piezoelectric element 65 (full length, width, and thickness). As a result, in a case where the voltage is applied to the pair of the electrode 651a and the electrode 651d in a state illustrated in FIG. 5B, the tip end portion (a portion with which the convex portion 67 is provided) of the piezoelectric motor 64 performs an operation (the elliptical motion) of turning clockwise as if drawing an ellipse in the drawing. In addition, in a case where the voltage is applied to the pair of the electrode 651b and the electrode 651c in a state illustrated in FIG. 5C, the tip end portion of the piezoelectric motor 64 performs the elliptical motion of turning counterclockwise in the drawing. The piezoelectric element 65 of the rear side has exactly the same configuration as that of the piezoelectric motor 64 of the front side.

The piezoelectric motor 64 drives the first link portion 3 which is a driven body by using such an elliptical motion.

That is, the elliptical motion is generated in a state in which the convex portion 67 of the piezoelectric motor 64 is pressed to an external edge portion 632a of the large disk portion 632 of the third rotor 63. Accordingly, the convex portion 67 moves from the left to the right (or from the right to the left) in a state of being pressed to the driven body when the piezoelectric motor 64 extends; on the other hand, the convex portion 67 returns back to the previous position in a state of being separated from the driven body when the piezoelectric motor 64 contracts, and the convex portion 67 repeats the above operations. As a result, the third rotor 63 rotates in one direction due to the friction force received from the convex portion 67. Then, such a rotating force is transferred via the small gear 631 of the third rotor 63, the large gear 622 of the second rotor, the small gear 621, and the first rotor 61 in order. Accordingly, it is possible to drive the first link portion 3 to be turned via the turning support portion 11.

In the finger joint driving device 1, it is possible to reliably drive the first link portion 3 to be turned with a simple configuration by using the piezoelectric element 65. In addition, the configuration using the piezoelectric element 65 contributes to miniaturization and thickness reduction of the finger joint driving device 1.

In addition, it is preferable that the piezoelectric motor 64 bend to the side in which the proximal interphalangeal joint 107 of the index finger 101 grasps so as to get a high resolution.

Meanwhile, the driving unit 6A functions for driving the first link portion 3 to be turned in the embodiment, but may function for driving the second link portion 4 to be turned. Similarly, in this case, it is possible to reliably drive the second link portion 4 to be turned and to contribute to miniaturization and thickness reduction of the finger joint driving device 1.

The control unit 10 controls the operation of the driving unit 6A based on a program which is recorded in advance. The control unit 10 is, for example, built into the second link portion 4 together with a battery (not shown) such as a button battery which supplies electric power to the driving unit 6A. Meanwhile, the configuration of the control unit 10 is not particularly limited. For example, it is possible to employ a configuration including a microprocessor and a memory.

As illustrated in FIG. 6 and FIG. 7, a pressure sensitive unit 7 is provided between the knuckle 102 of the index finger 101 and the first base portion 2. The pressure sensitive unit 7 includes a pressure sensor (a force detection unit) 8 and a contact portion 9 coming in contact with the knuckle 102 in the mounted state.

The pressure sensor 8 is formed into a plate shape and an upper surface 81 is fixed to the surface 21 of the first base portion 2. In addition, the pressure sensor 8 detects the force (hereinafter, referred to as "pressure force F") which is applied to the first base portion 2 from the knuckle 102. The pressure sensor is not particularly limited; for example, it is possible to use a pressure conductive rubber, a crystal-type pressure sensor, or the like. The pressure sensor 8 is electrically connected to the control unit 10.

As illustrated in FIG. 7, the contact portion 9 is configured to have a plate-shaped portion 91, a connecting portion 92, and a regulating portion 93.

The plate-shaped portion 91 is provided to face the first base portion 2 via the pressure sensor 8. In addition, the plate-shaped portion 91 is positioned between the pressure sensor 8 and the knuckle 102 in the mounted state. The size of the plate-shaped portion 91 is enough to include the pressure sensor 8 in a planar view.

A convex portion 911 which is projected upward is formed substantially in the middle of the plate-shaped portion 91. The convex portion 911 is a portion coming in contact with the pressure sensor 8 in the mounted state. The convex portion 911 is formed into a prism shape, and an apex portion 912 thereof is a plane surface. Due to the convex portion 911, it is possible to reliably press the pressure sensor onto the first base portion 2 in the mounted state.

A base end of the plate-shaped portion 91 is subjected to cantilever support by the connecting portion 92. In addition, a first engaging pawl 921 which is engaged with the regulating portion 93 is provided on the free end side (the finger end side) of the plate-shaped portion 91.

The connecting portion 92 serves for connecting the plate-shaped portion 91 to the first base portion 2. The connecting portion 92 is projected downward from the surface 21 of the first base portion 2. In addition, the lower end portion of the connecting portion 92 corresponds to the turning support portion 922 and is connected to the plate-shaped portion 91 via the turning support portion 922. Accordingly, the plate-shaped portion 91 can be turned with respect to the connecting portion 92.

The regulating portion 93 is provided on the free end side of the plate-shaped portion 91. The regulating portion 93 is projected downward from the surface 21 of the first base portion 2. In addition, a second engaging pawl 931 which is projected to the plate-shaped portion 91 side is provided on a lower end portion of the regulating portion 93. The second engaging pawl has a portion overlapping with the first engaging pawl 921 in a planar view of the plate-shaped portion 91, and is provided on the lower side of the first engaging pawl.

In an unused state in which the finger joint driving device 1 is not mounted on the index finger 101, it is assumed that the plate-shaped portion 91 turns counterclockwise by its own weight in FIG. 7, but it is possible to regulate the turning limit of the plate-shaped portion 91 by engaging the first engaging pawl 921 with the second engaging pawl 931. Therefore, it is possible that the plate-shaped portion 91 is prevented from inhibiting the mounting when switching from the unused state to the mounted state.

In addition, the contact portion 9 is separated from the pressure sensor 8 in the unused state. Accordingly, it is possible to prevent the unnecessary operation of the pressure sensor 8.

Meanwhile, a biasing portion may be provided on the turning support portion 922. The biasing portion biases the plate-shaped portion 91 so as to be turned counterclockwise in FIG. 7. Accordingly, in the unused state, it is possible to reliably maintain a state in which the pressure sensor 8 and the contact portion 9 are separated from each other.

Further, in the mounted state, the plate-shaped portion 91 is pressed by the finger to be turned clockwise in FIG. 7. Accordingly, the convex portion 911 comes in contact with the pressure sensor 8, and thus it is possible to detect pressure force F. Meanwhile, the pressure force F is assumed to be pressure force $F_1$ in a stationary state in which the index finger 101 remains stationary.

When the index finger 101 is bent in the stationary state, the pressure force F becomes pressure force $F_2$ which is smaller than the pressure force $F_1$. On the other hand, when the index finger 101 is stretched in a bent state, the pressure force F becomes greater than the pressure force $F_2$ and then returns to the pressure force $F_1$ when the index finger 101 is completely stretched.

Due to the change of the pressure force F with the bending and stretching of the finger, it is possible to recognize the movement of the finger.

Here, since the finger is relatively flexible, it is difficult to accurately detect the pressure force F. Thus, in the invention, the durometer hardness of the plate-shaped portion 91 which is measured based on JIS K 6253 is assumed to be equal to or greater than 50. Accordingly, it is possible to make the hardness of the plate-shaped portion 91 be reliably greater than the hardness of the index finger 101 (the average hardness of the general index finger in the embodiment). By interposing the plate-shaped portion 91 between the index finger 101 and the pressure sensor 8, it is possible to efficiently transfer the pressure force F to the pressure sensor 8. Accordingly, it is possible to accurately detect the pressure force F.

Meanwhile, the durometer hardness of the plate-shaped portion 91 which is measured based on JIS K 6253 is preferably equal to or greater than 80, and more preferably equal to or greater than 90 and less than 100. Accordingly, it is possible to more reliably achieve the above-described effect.

In addition, materials configuring the plate-shaped portion 91 (the contact portion 9) are not particularly limited; for example, various kinds of resin materials or various kinds of metallic materials can be used, but the resin material is preferably used.

In a case where the plate-shaped portion 91 (the contact portion 9) is configured from the resin material, the Rockwell hardness of the contact portion 9 which is measured based on JIS K 7202 is preferably equal to or greater than 65, and more preferably equal to or greater than 80, and particularly preferably equal to or greater than 105 and less than 130. Accordingly, it is possible to more reliably achieve the above-described effect.

Meanwhile, as the resin material, the following materials are included and can be used singly or in combination of two or more; polyolefins such as polyethylene, polypropylene, and ethylene-propylene copolymers, polyvinyl chloride, polystyrene, polyamide, polyimide, polycarbonate, poly-(4-methyl pentene-1), ionomer, acrylic resin, polymethyl methacrylate, acrylonitrile-butadiene-styrene copolymer (ABS resin), acrylonitrile-styrene copolymer (AS resin), butadiene-styrene copolymer, polyesters such as polyethylene terephthalate (PET) and polybutylene terephthalate (PBT), polyethers, polyether ketones (PEK), polyetheretherketone (PEEK), polyetherimide, polyacetal (POM), polyphenylene oxide, polysulfone, polyether sulfone, polyphenylene sulfide, polyarylate, aromatic polyester (liquid crystal polymer), polytetrafluoroethylene, polyvinylidene fluoride, and other fluorine-based resins, epoxy resins, phenolic resins, urea resins, melamine resins, silicone resins, polyurethane, or a copolymer having these as the main, blend, polymer alloy and the like.

As described above, according to the pressure sensitive unit 7, in a case where the index finger 101 is bent in the mounted state, it is possible to reliably and accurately detect the pressure force F. Thus, it is possible to accurately grasp whether the user wants to bend or stretch the index finger 101.

Next, the operation of the finger joint driving device 1 will be described.

In the state illustrated in FIG. 2, in the finger joint driving device 1, the first base portion 2 is mounted on the knuckle 102 of the index finger 101 and the second base portion 5 is mounted on the middle phalanx 103. Then, when the driving unit 6A is operated in this state as described above, as illustrated in FIG. 3, it is possible to turn the second link portion 4 in the counterclockwise direction in the drawing. Therefore, the middle phalanx 103 of the index finger 101 is pressed together with the second base portion 5 on the obliquely right downward side in FIG. 3. As a result, the proximal interphalangeal joint 107 of the index finger 101 is bent.

In addition, if the second link portion 4 is turned in the direction opposite to the above described turning direction from the state illustrated in FIG. 3, as illustrated in FIG. 2, the middle phalanx 103 of the index finger 101 is pulled together with the second base portion 5 on the obliquely left upward side in the drawings. As a result, the proximal interphalangeal joint 107 of the index finger 101 extends.

Further, if the proximal interphalangeal joint 107 is bent (or extends), the second base portion 5 is separated (or approaches with respect to) from the first base portion 2. However, as described above, since the second link portion 4 and the second base portion 5 are relatively movable, the second base portion 5 is quickly and smoothly separated (or approaches with respect to) from the first base portion 2. Accordingly, it is possible to easily bend the proximal interphalangeal joint 107, thereby reducing a burden to the index finger 101.

In addition, the user of the finger joint driving device 1 can bend and stretch the distal interphalangeal joint 109 of the index finger 101, a thumb, a middle finger, a ring finger, and a little finger which are not assisted by the finger joint driving device 1 separately from the proximal interphalangeal joint 107 of the index finger 101.

Further, for example, the finger joint driving device 1 can suppress the thickness of the entire device compared with a configuration in which the member which slides on the back of the hand 105 slides and thus the finger joint is allowed to bend and stretch (for example, refer to JP-A-2002-345861). Accordingly, when the user uses the finger joint driving device 1 mounted on the hand, it is possible to reduce the limitation of the movement of a user's hand.

In addition, since the second link portion 4 and the second base portion 5 are relatively movable in the middle phalanx 103 of the index finger 101 side, it is possible to mount the finger joint driving device 1 without depending on the length of the index finger 101, thereby realizing high versatility.

Meanwhile, in the finger joint driving device 1 in the mounted state, the first base portion 2 is disposed on the knuckle 102 of the index finger 101 and the second base portion 5 is disposed on the middle phalanx 103 in the embodiment; however, such a disposition is not limited. For example, in the mounted state, the first base portion 2 may be disposed on the back of the hand 105 and the second base portion 5 may be disposed on the knuckle 102 of the index finger 101. In this case, it is possible to bend and stretch the metacarpophalangeal joint (the third joint) 108 by the finger joint driving device 1. Additionally, in the mounted state, the first base portion 2 may be disposed on the middle phalanx 103 of the index finger 101 and the second base portion 5 may be disposed on the distal phalanx 104. In this case, it is possible to bend and stretch the distal interphalangeal joint (the first joint) 109 by the finger joint driving device 1. In addition, in the mounted state, the first base portion 2 may be disposed on the middle phalanx 103 of the index finger 101 and the second base portion 5 may be disposed on the side of the end portion of the finger, that is, the knuckle 102 of the wrist side from the first base portion 2. In this case, similar to the mounted state in the embodiment, it is possible to bend and stretch the proximal interphalangeal joint 107 by the finger joint driving device 1.

As described above, it is possible to preferentially assist the finger joint to be bent and stretched, and therefore, it is possible to flexibly perform various assist operations with response to the usage state.

Meanwhile, the finger joint driving device 1 is used in rehabilitation for a person, for example, who has trouble bending and stretching the finger due to an accident or illness, who has a weak grip, or who has weakened force because of age. For example, when the detected pressure force F is decreased, it is possible to determine that the user wants to bend the finger. In this case, by driving the finger joint driving device 1 in the direction the index finger 101 is trying to bend, the user can easily bend the index finger 101. On the other hand, when the pressure force F is increased, it is possible to determine that the user wants to stretch the index finger 101. In this case, by driving the finger joint driving device 1 in the direction the index finger 101 is trying to stretch, the user can easily stretch the index finger 101.

In addition, at the time of the aforementioned rehabilitation, the index finger 101 may be forcedly bent and stretched by driving the finger joint driving device in the mounted state. At this time, when the pressure force F detected by the pressure sensitive unit 7 exceeds a threshold which is set in advance, it is determined that a pressure force becomes an excessive burden to the user, and thus if the pressure force F exceeds the threshold, the driving of the finger joint driving device 1 is stopped. Accordingly, it is possible to prevent the excessive burden on the user during the rehabilitation.

Such an operation of the finger joint driving device is preferably recorded in advance in a memory of the control unit 10 as a program.

Second Embodiment

Figure 8:
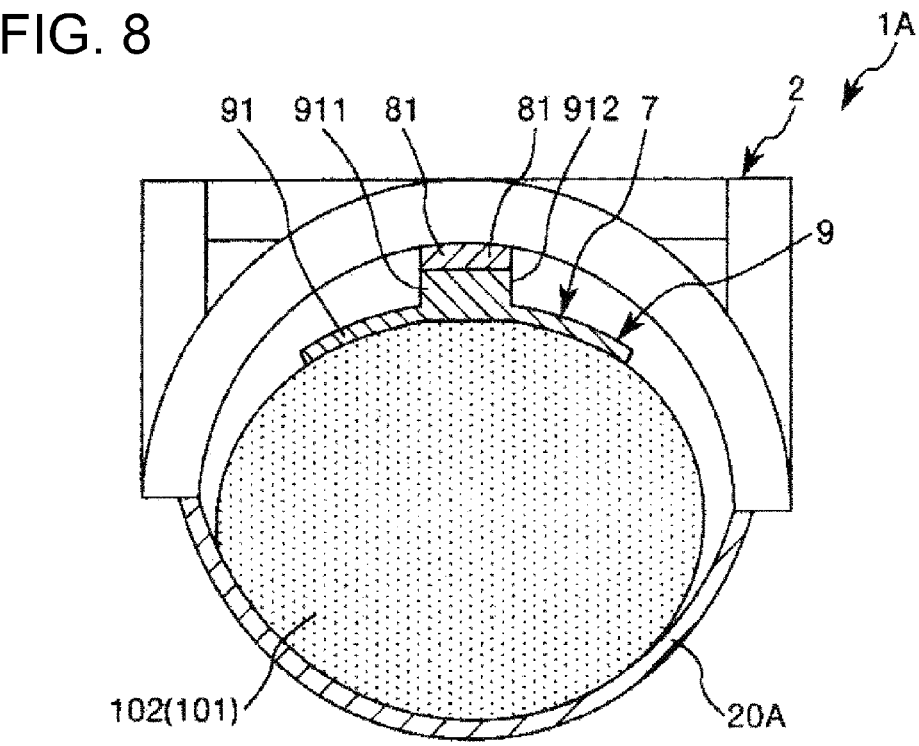
FIG. 8 is a longitudinal sectional view illustrating a usage state of a finger joint driving device (a second embodiment) according to the invention.

FIG. 8 is a longitudinal sectional view illustrating a usage state of a finger joint driving device (a second embodiment) according to the invention.

Hereinafter, a finger joint driving device of the second embodiment will be described with reference to FIG. 8, but the description will focus on the differences from the embodiments described above and the same matters will be omitted.

The description of the embodiment is the same as that of the first embodiment except for the configuration of the pressure sensitive unit.

As illustrated in FIG. 8, in a finger joint driving device 1A, the plate-shaped portion 91 is bent to one direction, that is, the first base portion 2 side in the mounted state. Accordingly, in the mounted state, the plate-shaped portion 91 follows the shape of the index finger 101. Therefore, the user can avoid feeling tightness and discomfort.

Meanwhile, an average of curvatures R of the plate-shaped portion 91 is preferably in the range of 1.0 to 6.0 and more preferably in the range of 2.5 to 4.5. Accordingly, it is possible to exhibit the above-described effect regardless of the individual differences of the user's index finger 101. Therefore, the finger joint driving device 1A is excellent in versatility.

Third Embodiment

Figure 9:
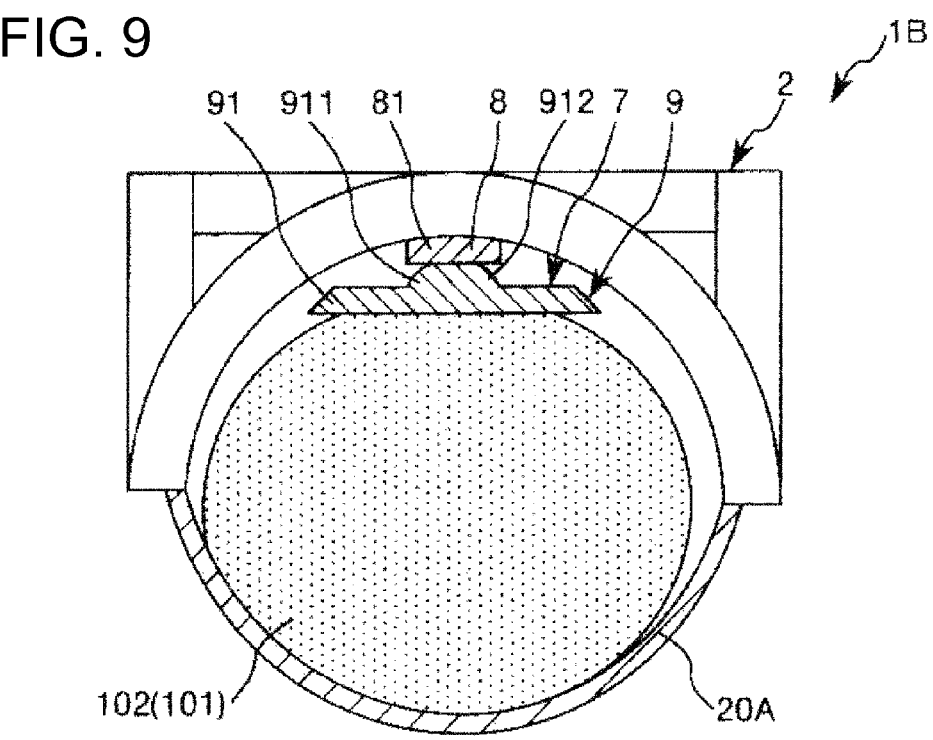
FIG. 9 is a longitudinal sectional view illustrating a usage state of a finger joint driving device (a third embodiment) according to the invention.

FIG. 9 is a longitudinal sectional view illustrating a usage state of a finger joint driving device (a third embodiment) according to the invention.

Hereinafter, a finger joint driving device of the third embodiment of the invention will be described with reference to FIG. 9, but the description will focus on the differences from the embodiments described above and the same matters will be omitted.

The description of the embodiment is the same as that of the first embodiment except for the configuration of the convex portion.

As illustrated in FIG. 9, in a finger joint driving device 1B, the convex portion 911 includes a curved surface 913 which is curved to the upper side, that is, the first base portion 2 in FIG. 9. Accordingly, it is possible to reduce a contact area of the pressure sensor 8 and the convex portion 911 as much as possible. Accordingly, it is possible to efficiently detect the pressure force F even in a case where the pressure force F is relatively small since the contact area is small.

With such a configuration, it is possible to improve detection accuracy of the pressure sensor 8.

Fourth Embodiment

Figure 10:
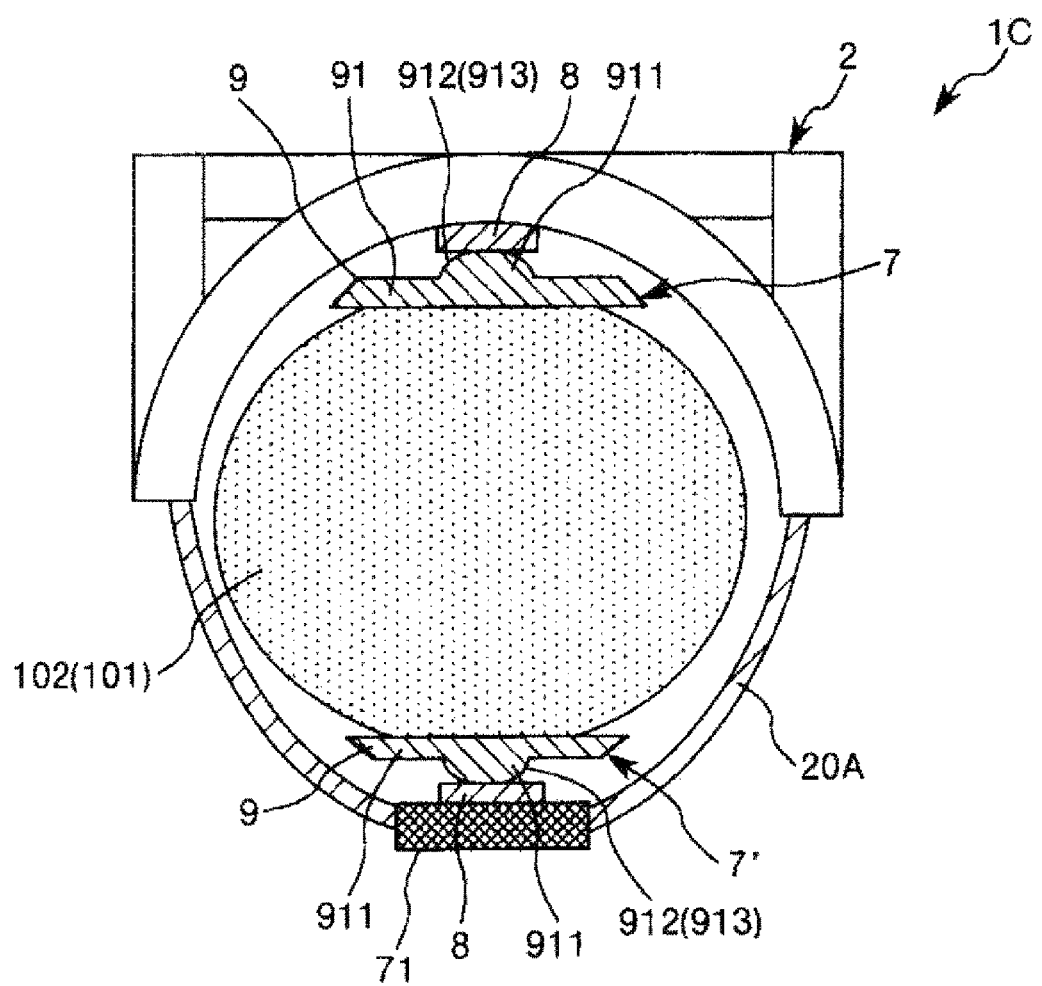
FIG. 10 is a longitudinal sectional view illustrating a usage state of a finger joint driving device (a fourth embodiment) according to the invention.

FIG. 10 is a longitudinal sectional view illustrating a usage state of a finger joint driving device (a fourth embodiment).

Hereinafter, a finger joint driving device of the fourth embodiment will be described with reference to FIG. 10, but the description will focus on the differences from the embodiments described above and the same matters will be omitted.

The description of the embodiment is the same as that of the third embodiment except for the installation number of the pressure sensitive unit.

As illustrated in FIG. 10, a finger joint driving device 1C is provided with another pressure sensitive unit 7' in addition to the pressure sensitive unit 7.

The pressure sensitive unit 7' is provided on the side opposite to the pressure sensitive unit 7 via the knuckle 102, that is, provided on the mounting band 20A side in the mounted state. The pressure sensitive unit 7' is disposed such that the convex portion 911 is projected toward the palm of the hand.

In addition, a hard plate piece 71 is provided in the middle of the lateral direction of the mounting band 20A. In the mounted state, the pressure sensor 8 is interposed between the hard plate piece 71 and the convex portion 911. Note that the hardness of the plate piece 71 is preferably the same as the hardness of the first base portion 2.

In the finger joint driving device 1C, when the index finger 101 is bent, the pressure force F which is detected by the pressure sensor 8 of the pressure sensitive unit 7 is decreased whereas the pressure force F which is detected by the pressure sensor 8 of the pressure sensitive unit 7' is increased. On the other hand, when the index finger 101 is stretched in a state in which the index finger 101 is bent, the pressure force F which is detected by the pressure sensor 8 of the pressure sensitive unit 7 is increased whereas the pressure force F which is detected by the pressure sensor 8 of the pressure sensitive unit 7' is decreased.

In the finger joint driving device 1C, in a case where the index finger 101 is bent and stretched, the movement of the index finger 101 is determined based on a difference of the pressure force F which is detected by each of the pressure sensors 8. Accordingly, the movement of the index finger 101 is determined based on substantially twice the pressure force F compared with a case in which one of the pressure sensors 8 is omitted. Therefore, even in a case where the pressure force F is relatively small, it is possible to more accurately detect the pressure force F.

As described above, embodiments of the finger joint driving device according to the invention are described; however, the invention is not limited thereto, each portion configuring the finger joint driving device can be replaced with that of an arbitrary configuration capable of exhibiting the same function. In addition, arbitrary components may be added to the invention.

In addition, the finger joint driving device according to the invention may be a combination of any two or more configurations (features) in the embodiments described above.

Further, the convex portion is provided in the plate-shaped portion (the contact portion) in the embodiments; however, the invention is not limited thereto. For example, the convex portion may be provided on the finger mounting portion, or may be provided on the contact portion and the finger mounting portion. In addition, a member which functions as a spacer separately is installed on the contact portion and the finger mounting portion by omitting the convex portions.

In addition, in the embodiment, the pressure sensitive unit is provided on the first base portion, but the invention is not limited thereto. For example, the pressure sensitive unit may be provided on the second base portion (the fourth member) and may be provided on both of the first base portion and the second base portion.

In addition, the mounting position of the finger joint driving device with respect to the hand is the index finger in the embodiment, but the invention is not limited thereto. For example, the position may be a thumb, a middle finger, a ring finger, or a little finger.

In addition, the first driving unit can serve for driving the second member (the first link portion) and the third member (the second link portion) to be turned in the respective embodiments, but the first driving unit can also serve for driving the fourth member (the second base portion) to approach with respect to and to be separated from with respect to the first member (the first base portion).

In addition, the second driving unit can serve for driving the fifth member (the third link portion) and the sixth member (the fourth link portion) to be turned in the second embodiment, and the second driving unit can also serve for driving the seventh member (the third base portion) to approach with respect to and to be separated from with respect to the fourth member (the second base portion).

The entire disclosure of Japanese Patent Application No. 2014-042452, filed Mar. 5, 2014 is expressly incorporated by reference herein.

What is claimed is:

1. A finger joint driving device configured for use on a finger, the finger joint driving device comprising:
   a finger mounting portion that is configured to be mounted on the finger;
   a force detection unit that is configured to be provided between the finger mounting portion and the finger when the finger mounting portion is mounted on the finger; and
   a contact portion that is configured to be provided between the force detection unit and the finger and comes in contact with the force detection unit when the finger mounting portion is mounted on the finger,
   wherein durometer hardness of the contact portion which is measured based on JIS K 6253 is equal to or greater than 50.

2. The finger joint driving device according to claim 1, wherein Rockwell hardness of the contact portion which is measured based on JIS K 7202 is equal to or greater than 80.

3. The finger joint driving device according to claim 1, wherein at least one of the contact portion and the finger mounting portion includes a convex portion projected to the force detection unit.

4. The finger joint driving device according to claim 3, wherein the convex portion has a curved surface which is curved toward the force detection unit.

5. The finger joint driving device according to claim 1, wherein the contact portion is formed into a plate shape which is curved toward one direction.

6. The finger joint driving device according to claim 1, wherein the force detection unit and the contact portion are configured to be positioned on a back of a hand of the finger in the mounted state.

7. The finger joint driving device according to claim 1, wherein the finger mounting portion includes a finger mounting portion main body that is configured to be positioned on a back of a hand of the finger and a fixing portion that is configured to be positioned on a palm of the hand of the finger to fix the finger mounting portion main body to the finger when the finger mounting portion is mounted on the finger.

8. The finger joint driving device according to claim 7, further comprising another force detection unit and another contact portion such that there are a pair of the force detection units and a pair of the contact portions,
   wherein the pair of the force detection units and the pair of the contact portions are configured to be provided via the finger when the finger mounting portion is mounted on the finger, and
   wherein one of the force detection units and one of the contact portions are provided on a finger mounting portion main body side, and the other of the force detection units and the other of the contact portions are provided on a fixing portion side.

* * * * *